United States Patent [19]

Fuluhata et al.

[11] Patent Number: 5,656,729
[45] Date of Patent: Aug. 12, 1997

[54] METHOD FOR HIGHLY PURIFYING HUMAN SERUM ALBUMIN

[75] Inventors: Naoto Fuluhata; Akinori Sumi; Takao Ohmura, all of Hirakata, Japan

[73] Assignee: The Green Cross Corporation, Osaka, Japan

[21] Appl. No.: 374,719

[22] PCT Filed: Jul. 26, 1993

[86] PCT No.: PCT/JP93/01048

§ 371 Date: Apr. 28, 1995

§ 102(e) Date: Apr. 28, 1995

[87] PCT Pub. No.: WO94/03626

PCT Pub. Date: Feb. 17, 1994

[30] Foreign Application Priority Data

Jul. 31, 1992 [JP] Japan ............................ 4-205637

[51] Int. Cl.$^6$ ............................................ C12P 21/00
[52] U.S. Cl. ............................. 530/364; 530/413
[58] Field of Search ...................................... 530/364

[56] References Cited

U.S. PATENT DOCUMENTS

| 5,169,936 | 12/1992 | Staples et al. | 530/350 |
| 5,330,901 | 7/1994 | Prevatt et al. | 435/69.6 |
| 5,440,018 | 8/1995 | Ohmura et al. | 530/363 |

FOREIGN PATENT DOCUMENTS 9012803  11/1990  WIPO .

OTHER PUBLICATIONS

Hansson et al., J. Chromatog. 215:333–339 (1981).
Sulkowski, Trends Biotechnol. 3:1–7 (1985).
Andersson et al., Bioseparation 2:15–22 (1991).
Andersson et al., Cancer Res. 47:3624–3626 (1987).
Abstract No. 88059400, *Database Medline*, (Aug. 21, 1987).
Abstract No. 92207443, *Database Medline*, (Sep.–Oct. 1991).

*Primary Examiner*—Keith D. Hendricks
*Assistant Examiner*—Eric Grimes
*Attorney, Agent, or Firm*—Sughrue, Mion, Zinn, Macpeak & Seas

[57] ABSTRACT

A method for highly purifying human serum albumin (HSA), which comprises bringing a fraction containing HSA produced by genetic engineering into contact with a chelating chromatography carrier bound with copper ions, and eluting the HSA adsorbed by the carrier with a buffer containing ammonium chloride as an atagonist and having a pH of about 5–7.

According to the method of the present invention, a component derived from yeast, which cannot be sufficiently removed by conventional purification methods for HSA produced by genetic engineering, can be removed from HSA produced by genetic engineering, and a highly purified HSA can be provided.

13 Claims, 2 Drawing Sheets

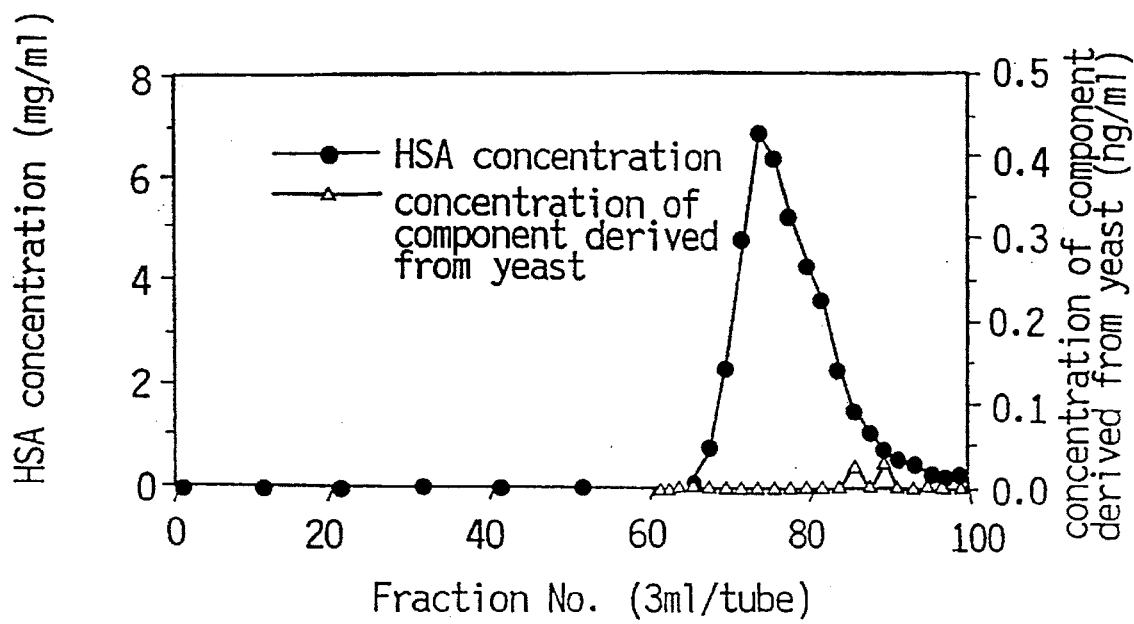
Cu-chelating chromatography of r-HSA (pH6.0)
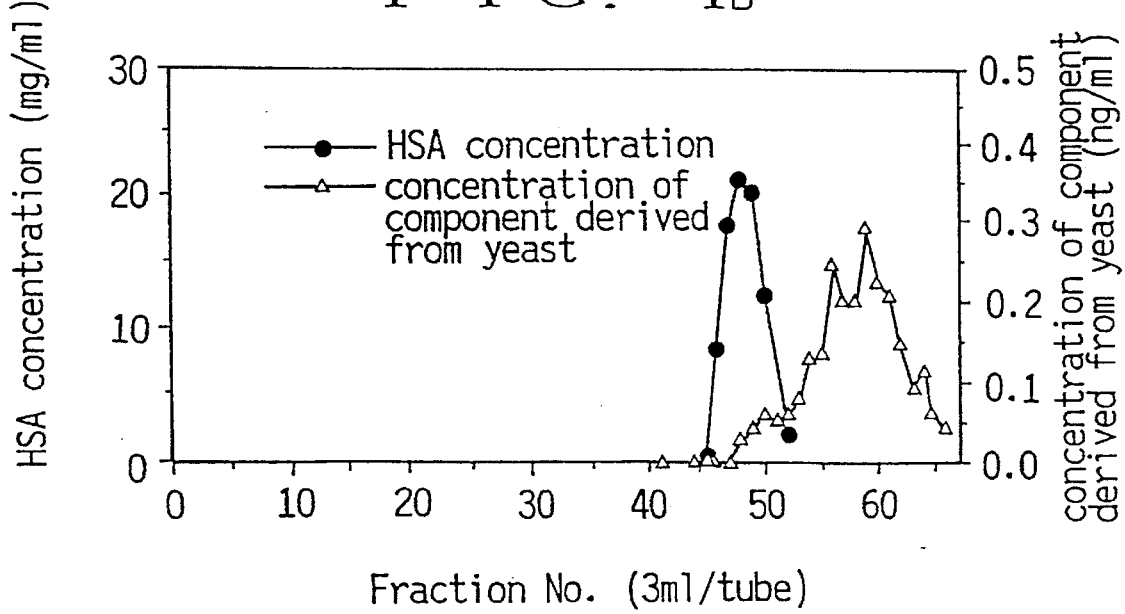
Cu-chelating chromatography of r-HSA (pH7.0)

Cu-chelating chromatography of r-HSA (pH6.0)

Cu-chelating chromatography of r-HSA (pH7.0)

METHOD FOR HIGHLY PURIFYING HUMAN SERUM ALBUMIN

TECHNICAL FIELD

The present invention relates to a method for highly purifying human serum albumin, which is characterized by subjecting human serum albumin produced by genetic engineering to Cu-chelating chromatography.

BACKGROUND ART

An albumin, particularly human serum albumin (hereinafter also referred to as HSA) is an important component constituting protein in plasma. This protein is produced in liver, and is mainly responsible for sustaining normal osmotic pressure of blood flow. Also, it functions as a carrier for various serum molecules. HSA is administered in a variety of clinical situations. For example, when HSA is administered to a patient suffering from shock or ambustion, it functions to recover blood volume to its original level, thereby improving some symptoms relating to trauma. For this effect, HSA is frequently administered. Also, patients suffering from hypoproteinemia or fetal erythroblastosis may need treatments with HSA.

As exemplified, the basic significance of HSA administration is prominent in the treatment of symptoms accompanying loss of fluids from blood vessels, as in surgery, shock, burn, or hypoproteinemia which causes edema.

At present, HSA is produced mainly by fractionation of blood. This production method is uneconomical, and besides, it poses a problem that the supply of the blood is not always assured. Moreover, the blood may contain undesirable substances such as hepatitis viruses. Accordingly, the development of a substitute raw material for HSA will be greatly advantageous.

In the meantime, the advent of the recombinant DNA technique has enabled production of various useful polypeptides by microorganisms, and many mammalian polypeptides have been already produced by various kinds of microorganisms. A technique permitting large-scale production of HSA by utilizing genetic engineering and purification thereof is being established.

Methods for isolating and purifying HSA from plasma have been variously studied and have seen practical application. For example, Cohn's ethanol fractionation, PEG fractionation and ammonium sulfate fractionation are known. In recent years, a combined method of treatment with anion exchanger and heat treatment at 60° C. for 10.hours (Japanese Patent Unexamined Publication No. 191226/1990), and a combined method of treatment with anion exchanger, treatment with cation exchanger and heat treatment at 60° C. for 10 hours (Japanese Patent Unexamined Publication No. 17123/1991) have been developed.

While the purification of recombinant HSA (r-HSA) obtained by genetic engineering has been studied in a variety of ways, the study has not yet succeeded in removing contaminant components derived from yeast. The presence of such component derived from yeast has a probability of causing problems of antigenicity, since the component is a foreign substance to living organisms. That is, the purity of the recombinant type proteins is insufficient and the contaminant component derived from yeast needs to be removed further.

DISCLOSURE OF THE INVENTION

An object of the present invention is to remove, when producing HSA by genetic engineering, the aforementioned component derived from yeast, which cannot be sufficiently removed by conventional methods for purifying HSA produced by genetic engineering, and to provide a highly purified HSA.

In view of the above situation, the present inventors conducted various studies for achieving the object as described, and have found that Cu-chelating chromatography of HSA for purification thereof, when obtaining HSA by genetic engineering, results in advanced removal of the contaminant components derived from yeast, which resulted in the completion of the invention.

Accordingly, the present invention relates to a method for highly purifying human serum albumin, which comprises subjecting a fraction containing human serum albumin produced by genetic engineering, to Cu-chelating chromatography, and more specifically, the present invention relates to a method for highly purifying human serum albumin produced by genetic engineering, which comprises applying a fraction containing r-HSA to a chelating resin column bound with copper ions and eluting the adsorbed component with a buffer containing ammonium chloride as an atagonist and having a pH of 5–7.

BRIEF DESCRIPTION OF DRAWINGS

FIG. 1 shows r-HSA monomer concentration and concentration of a component derived from yeast in each eluted fraction in Example 1.

DETAILED DESCRIPTION OF THE INVENTION

Figure 2A:
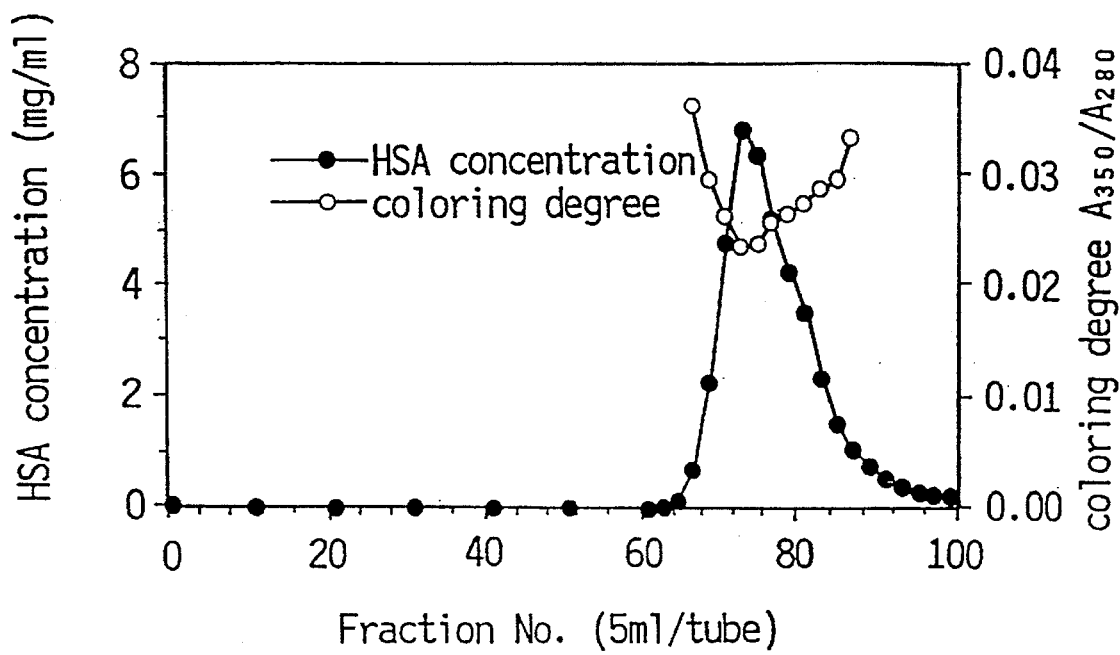
FIG. 2 shows r-HSA monomer concentration and $A_{350}/A_{280}$ value of each eluted fraction in Example 1.

The present invention relates to a method for highly purifying human serum albumin for the production of HSA by genetic engineering, and said HSA is produced by culturing cells (e.g. *Escherichia coli*, yeast, *Bacillus subtilis*, *Aspergillus*, animal cells) capable of expressing HSA by genetic engineering, followed by extracellular expression (secretory expression).

1. HSA produced by genetic engineering

The HSA produced by genetic engineering in the present invention is an HSA produced by an HSA-producing host prepared by genetic engineering. The HSA-producing host is subject to no particular limitation as long as it is prepared by genetic engineering, and any host whether disclosed in known literatures or to be developed in the future may be used appropriately. Specific examples of the hosts are those imparted with HSA producibility by genetic engineering, such as *Escherichia coli*, yeast and *Bacillus subtilis*, and animal cells. Particularly in the present invention, the use of a yeast, specifically the genus *Saccharomyces* (e.g. *Saccharomyces cerevisiae*) or the genus *Pichia* (e.g. *Pichia pastoris*) as a host is desirable. Also, auxotroph strains and antibiotic sensitive strains can be used. In addition, the *Saccharomyces cerevisiae* AH22 strain (a, *his* 4, *leu* 2, *can* 1) and *Pichia pastoris* GTS115 strain (*his* 4) can be preferably used.

The method for the preparation of these HSA-producing hosts, the method for producing HSA by culturing the hosts, and the method for the separation and harvesting of HSA from cultures may be known or those analogous thereto. For example, the methods for the preparation of an HSA-producing host (or HSA-producing strain) include a method wherein a known human serum albumin gene is used (Japanese Patent Unexamined Publication Nos. 56684/1983, 90515/1983, 150517/1983), a method wherein a new human serum albumin gene is used (Japanese Patent Unexamined Publication Nos. 29985/1987, 98486/1989), a method wherein a synthetic signal sequence is used (Japanese Patent Unexamined Publication No. 240191/1989), a method wherein serum albumin signal sequence is used (Japanese Patent Unexamined Publication No. 167095/1990), a method wherein a recombinant plasmid is incorporated on chromosome (Japanese Patent Unexamined Publication No. 72889/1991), a method wherein hosts are fused (Japanese Patent Unexamined Publication No. 53877/1991), a method wherein mutation is caused in a medium containing methanol, a method wherein mutant AOX2 promoter is used (EP-A-566040, Japanese Patent Unexamined Publication No. 299984/1992), an expression of HSA by *Bacillus subtilis* (Japanese Patent Unexamined Publication No. 25133/1987), an expression of HSA with yeast (Japanese Patent Unexamined Publication Nos. 41487/1985, 39576/1988 and 74493/1988), an expression of HSA with Pichia (Japanese Patent Unexamined Publication No. 104290/1990), and the like.

Of the methods mentioned above, the method wherein mutation is caused in a medium containing methanol comprises the following steps. That is, a plasmid having a transcription unit, where HSA is expressed under the control of $AOX_1$ promoter, is introduced into a suitable host, preferably a Pichia yeast, specifically into an $AOX_1$ gene region of GTS115 strain (NRRL deposit No. Y-15851) by a conventional method to obtain a transformant (see Japanese Patent Unexamined Publication No. 104290/1990). This transformant shows poor growth in a medium containing methanol. Then, this transformant is cultured in a medium containing methanol to cause mutation, and only the strains which show rapid growth are collected. The methanol concentration is about 0.0001–5%, and the medium may be artificial or natural. Incubation is conducted at 15°–40° C. for about 1–1000 hours.

The methods for culturing an HSA-producing host, namely, production method for HSA, include a method wherein high concentration cells and yield products are obtained by supplying a suitably small amount of high concentration glucose, etc. by a fed-batch culture so as to avoid an inhibition effect caused by high concentration substrate on the yielded cells (Japanese Patent Unexamined Publication No. 83595/1991), a method wherein HSA production is enhanced by adding fatty acid in medium (Japanese Patent Unexamined Publication No. 293495/1992), and other methods, besides the methods described in the above publications.

The methods for the separation and harvesting of HSA include, for example, inactivation of protease by heat treatment (Japanese Patent Unexamined Publication No. 103188/1992) and suppression of coloring by separating HSA from coloring components with the use of at least one member of the group of anion exchanger, hydrophobic carrier, and active charcoal (Japanese Patent Unexamined Publication No. 54198/1992).

The medium to be used for the culture of a transformant host is a medium known in this field, which has been supplemented with a fatty acid having 10–26 carbon atoms or its salt, and culture can be conducted by a conventional method. The medium may be synthetic or natural, with preference given to a liquid medium. For example, synthetic medium may contain various sugars as carbon sources; urea, ammonium salt, nitrate, etc. as nitrogen sources; various vitamins and nucleotide as micronutrients; and Mg, Ca, Fe, Na, K, Mn, Co, Cu, etc. as inorganic salts, and is exemplified by YNB liquid medium [0.7% yeast nitrogen base (manufactured by Difco), 2% glucose]. Examples of natural medium include YPD liquid medium [1% yeast extract (manufactured by Difco), 2% Bacto-peptone (manufactured by Difco), 2% glucose]. The pH of the medium may be neutral, weak basic, or weak acidic. When a host utilizes methanol, a medium containing methanol can be used. In this case, the methanol concentration is about 0.01–5%.

The incubation temperature is preferably 15°–43° C. (20°–30° C. for yeasts, and 20°–37° C. for bacteria). The incubation is conducted for about 1 to 1,000 hours, under aeration, by batch culture, fed-batch culture, or continuous culture, by allowing to stand, shaking, or stirring.

Preculture in advance of main culture is preferable, wherein used is, for example, YNB liquid medium or YPD liquid medium. The preculture is conducted for 10 to 100 hours at 30° C. for yeasts and 37° C. for bacteria.

After the culture, HSA is harvested from culture filtrate or cells by known separation and purification methods.

After harvesting, the HSA is subjected to purification and treated according to the present invention alone or in combination with other purification methods.

2. Purification of HSA

The step for purifying HSA according to the present invention is preferably performed at a desired stage during the purification step conventionally performed for HSA produced by genetic engineering, particularly at the final stage, more preferably at the final stage of the steps comprising the following steps (1) to (7), i.e., after anion exchange chromatography.

(1) treatment of a culture supernatant of human serum albumin-producing host cells, using ultrafiltration membranes having a fractional molecular weight of from 100,000 to 500,000 and from 1,000 to 50,000;

(2) heat treatment at 50°–70° C. for 30 minutes to 5 hours;

(3) treatment with an acid at a pH of 3–5;

(4) treatment with an ultrafiltration membrane having a fractional molecular weight of from 100,000 to 500,000;

(5) contacting the fraction with a cation exchanger under the conditions of pH 3–5 and a salt concentration of 0.01–0.2M and eluting under the conditions of pH 8–10 and a salt concentration of 0.2–0.5M;

(6) contacting the eluate with a carrier for hydrophobic chromatography under the conditions of pH 6–8 and a salt concentration of 0.01–0.5M to collect an unadsorbed fraction; and (7) contacting the fraction with an anion exchanger under the conditions of pH 6–8 and a salt concentration of 0.01–0.1M to collect an unadsorbed fraction.

The above-mentioned steps may include, in place of the aforementioned step (6), a step of contacting the eluate with a carrier for hydrophobic chromatography under the conditions of pH 6–8 and salt concentration of 1–3M and then eluting under the conditions of pH 6–8 and salt concentration of 0.01–0.5M; a step of contacting the fraction with an anion exchanger under the conditions of pH 6–8 and salt concentration of 0.001–0.05M and then eluting under the conditions of pH 6–8 and salt concentration of 0.05–1M, in place of the aforementioned step (7); and a step of salting out under the conditions of pH 3–5 and salt concentration of 0.5–3M to collect a precipitate fraction, between the aforementioned steps (5) and (6), (6) and (7) or after (7).

3. Treatment of HSA by Cu-chelating chromatography

The treatment of HSA by Cu-chelating chromatography of the present invention is preferably incorporated in the final stage of the aforementioned purification steps and comprises contacting the fraction containing HSA with a chelating resin bound with $Cu^{2+}$, which is prepared by passing a solution containing $Cu^{2+}$, such as a $CuSO_4$ solution.

The carrier of chelating resin is subject to no particular limitation as long as it is a conventional insoluble carrier, and is exemplified by hydrophilic vinyl polymer, crosslinked dextran (trademark Sephadex), agarose (trademark Sepharose) and cellulose (trademark Cellulofine). The ligand moiety is exemplified by iminodiacetic acid. Said chelating resin may be any commercially available one for metal chelating affinity chromatography, such as AF-chelating Toyopearl 650 (manufactured by Toso), Chelating Sepharose 6B (manufactured by Pharmacia), Chelating Sepharose FF (manufactured by Pharmacia) and Chelating Cellulofine (manufactured by Seikagaku Kogyo).

The conditions for treating with a chelating resin are preferably as follows.

By linear gradient method

First, a chelating resin bound with $Cu^{2+}$ is equilibrated and washed. A buffer having a pH of about 5–7 and a salt concentration of 0.1–1M is used for the equilibration and washing. Specifically, a buffer (pH 5–7) of 10–100 mM acetate, phosphate or Tris-HCl supplemented with 0.1–1M sodium chloride is exemplified. Then, the fraction containing HSA is applied onto the chelating resin bound with $Cu^{2+}$ to allow separation and elution of HSA by the linear gradient method with the use of the aforementioned buffer containing an antagonist. Examples of the antagonist include ammonium chloride, imidazole, histidine, cysteine, glycine and histamine. The maximum concentration for linear gradient elution is about 1–3M for ammonium chloride and 0.01–0.1M for other antagonists.

By Pass method

First, a chelating resin bound with $Cu^{2+}$ is equilibrated and washed. A buffer having a pH of about 5–7 and a salt concentration of 0.1–1M, which contains an antagonist, is used for equilibrating and washing. The antagonist is exemplified by those mentioned above. Specific examples of the buffer include buffers (pH 5–7) of 10–100 mM acetate, phosphate or Tris-HCl supplemented with 0.1–1M sodium chloride. Then, the fraction containing HSA is applied onto the chelating resin bound with $Cu^{2+}$ to collect an unadsorbed fraction. Preferably, a system wherein a column of a chelating resin not bound with $Cu^{2+}$, which has been equilibrated with the aforementioned buffer having a pH of about 5–7 and a salt concentration of 0.1–1M and containing an antagonist, is connected next to the chelating resin column bound with $Cu^{2+}$, is used for purifying HSA.

The ratio of HSA and the chelating resin bound with $Cu^{2+}$ is 0.001–0.1 ml, preferably 0.002–0.01 ml of the resin relative to 1 mg of HSA.

The purity of the HSA obtained by the aforementioned steps [(1)–(7), salting out and Cu-chelating chromatography inclusive] as determined by ELISA is about $1 \times 10^{-9} - 5 \times 10^{-8}$ (best value: $2.78 \times 10^{-9}$, component derived from yeast/r-HSA, which is about 100 times higher than the purity before the treatment by Cu-chelating chromatography.

4. Formulation into preparation

The HSA thus obtained is formulated into a preparation by a known method, such as ultrafiltration, addition of stabilizers, sterilization by filtration, partition or lyophilization. The HSA preparation thus formulated can be used in clinical situations as injections, like the HSA preparation derived from plasma. Also, the HSA is usable as a stabilizer, carrier or vehicle for pharmaceuticals.

EFFECTS OF THE INVENTION

According to the present invention, a component derived from yeast, which cannot be sufficiently removed by conventional methods for purifying HSA produced by genetic engineering, can be removed from HSA produced by genetic engineering, and a highly purified HSA having a purity recommended by WHO (World Health Organization) as a recombinant type medicament, can be provided. It is also expected that removal of the component derived from yeast causes elimination of antigenicity, which in turn results in suppression of side effects such as allergy.

EXAMPLES

The present invention is hereinafter described in detail by referring to examples, to which the present invention is not limited.

Reference Example 1

Culture of HSA-producing host 1. Strain used: *Pichia Pastoris* GCP101

PC4130 can be obtained by replacing the AOX1 gone region of *Pichia pastoris* GTS115 (*his* 4) with the fragments cleaved with Not 1 of plasmid pPGP1 having a transcription unit where HSA expresses under the control of AOX1 promoter, by the method as described in Japanese Patent Unexamined Publication No. 104290/1990. Due to the absence of the AOX1 gone, this strain shows poor growth in a medium containing methanol as a carbon source (Mut-strain).

PC4130 was inoculated into 3 ml of YPD medium (1% yeast extract, 2% Baeto-peptone, 2% glucose), and 24 hours later, it was inoculated into 50 ml of YPD medium at a concentration that made the initial $OD_{540}$ 0.1. After incubation at 30° C. for 3 days, it was inoculated into 50 ml of YPD medium at a concentration that made the initial $OD_{540}$ 0.1. The same subculture was repeated every three days. At every subculture, cells were diluted with sterilized water to make the cell concentration $10^7$ cells/plate, and coated on a 2% MeOH-YNB w/o a. a. plate (0.7% yeast nitrogen base without amino acid, 2% methanol, 1.5% agar powder). After incubation at 30° C. for 5 days, formation of colony was checked. Twenty colonies were formed on a 2% MeOH-YNB w/o a. a. plate coated with cells after subculture for 12 days. Mut- strain hardly grew on this plate, but Mut+ strain could grow. That is, the colony formation on this plate indicates enhanced utilization of methanol, and it also indicates that a strain converted to Mut+ was obtained. One of the colonies formed was appropriately diluted with sterilized water, and spread on a 2% MeOH-YNB w/o a. a. plate into a single colony, which was named GCP101.

2. Culture of cells
   (pre-preculture)

One ml from glycerol frozen stock was inoculated into 200 ml of YPD medium (Table 1) in a 1,000 ml Erlenmeyer flask equipped with baffles, and subjected to shaking culture at 30° C. for 24 hours.

TABLE 1

| YPD medium composition | |
|---|---|
| Component | concentration (g/l) |
| Yeast extract | 10 |
| Peptone | 20 |
| Glucose | 20 |

(Preculture)

The pre-preculture was inoculated into YPD medium (5 l) in a 10 l jar fermenter and subjected to aerobic culture for 24 hours. The culture temperature was 30° C. and aeration rate was 5 l/min. The pH was not regulated in the preculture.

(main culture)

The preculture was inoculated into a medium (250 l, Table 2) for batch culture and subjected to aerobic culture using a 1,200 l fermenter. The pressure in the tank was 0.5 kg/cm$^2$ and the maximum aeration was 800 N-l/min. The batch culture was started by controlling the agitation speed in such a manner that maintains the concentration of dissolved oxygen at about 50–30% of the saturation concentration of the dissolved oxygen. A feed medium (Table 3) was added starting from the point when glycerol in the medium was consumed in the batch culture. The addition of the feed medium was controlled by a computer and high density culture was performed while controlling methanol, so that it would not accumulate in the medium. The pH was adjusted to a constant pH of 5.85 by the addition of 28% aqueous ammonia. Antifoaming was performed by adding 0.30 ml/l of an antifoaming agent (Adecanol, manufactured by Asahi Denka Kogyo) at the initiation of the batch culture and by adding a small amount thereof as necessary.

TABLE 2

Composition of medium for batch culture

| Component | |
|---|---|
| | concentration (/l) |
| Glycerol | 50.0 g |
| H$_3$PO$_4$ (85%) | 14.0 ml |
| CaSO$_4$.2H$_2$O | 0.6 g |
| K$_2$SO$_4$ | 9.5 g |
| MgSO$_4$.7H$_2$O | 7.8 g |
| KOH | 2.6 g |
| Biotin solution (*1) | 1.6 ml |
| YTM solution (*2) | 4.4 ml |
| | concentration (g/l) |
| FeSO$_4$.7H$_2$O | 65.0 |
| CuSO$_4$.5H$_2$O | 6.0 |
| ZnSO$_4$.7H$_2$O | 20.0 |
| MnSO$_4$.4–5H$_2$O | 3.0 |
| H$_2$SO$_4$ | 5.0 (ml/l) |

Note
(*1) Biotin solution 0.2 g/l
(*2) YTM solution

TABLE 3

Composition of feed medium

| Component | amount |
|---|---|
| YTM solution | 2 ml |
| Methanol | 1,000 ml |

Reference Example 2

Using the AOX2 promoter [mutant type, a wild type AOX2 promoter (YEAST, 5, 167–177 (1988) or Mol. Cell Biol., 9, 1316–1323 (1989)) mutated by substituting the 255th nucleotide, T, upstream of initiation codon with C] isolated from the GCP101 strain in Reference Example 1, an HSA expression plasmid pMM042 was constructed and introduced into *Pichia pastoris* GTS115 to give a transformant UHG42-3 (Japanese Patent Unexamined Publication No. 299984/1992). The UHG42-3 strain was cultured according to Reference Example 1 to produce HSA.

Reference Example 3

Purification of HSA (i) Separation of culture supernatant—membrane fractionation (II)

A supernatant was separated by compressing about 800 l of the culture obtained in Reference Example 1 or 2. The culture supernatant was treated with an ultrafiltration membrane having a fractional molecular weight of 300,000. Then, the mixture was concentrated to about 80 l using an ultrafiltration membrane having a fractional molecular weight of 30,000 [membrane fractionation (I)].

The concentrated solution was heat-treated at 60° C. for 3 hours, rapidly cooled to about 15° C., adjusted to pH 4.5 and treated again with an ultrafiltration membrane having a fractional molecular weight of 300,000 [membrane fractionation (II)]. The buffer in the albumin solution was changed to 50 mM acetate buffer, pH 4.5, containing 50 mM sodium chloride by the use of an ultrafiltration membrane having a fractional molecular weight of 30,000.

(ii) Treatment with cation exchanger

The albumin was adsorbed by S-Sepharose equilibrated with 50 mM acetate buffer, pH 4.5, containing 50 mM sodium chloride, and the column was sufficiently Washed with the same buffer. Then, the albumin was eluted with 0.1M phosphate buffer, pH 9, containing 0.3M sodium chloride.

(iii) Treatment by hydrophobic chromatography

The albumin solution eluted from the S-Sepharose column was applied to a column packed with Phenyl Cellulofine equilibrated with 50 mM phosphate buffer, pH 6.8, containing 0.15M sodium chloride. Under these conditions, the albumin passed through the column without being adsorbed by Phenyl Cellulofine.

The albumin which passed through the column was concentrated to about 50 l by the use of an ultrafiltration membrane having a fractional molecular weight of 30,000 and the buffer in the albumin solution was changed to 50 mM phosphate buffer, pH 6.8.

(iv) Treatment with anion exchanger

After the treatment by hydrophobic chromatography, concentration and exchange of buffer, the albumin solution was applied onto a column packed with DEAE-Sepharose equilibrated with 50 mM phosphate buffer, pH 6.8. Under these conditions, the albumin passed through the column without being adsorbed by DEAE-Sepharose.

Example 1

A 5 mg/ml CuSO$_4$ solution was poured on a Chelating Sepharose FF Column ($\phi$16×15 cm, 30 ml) previously washed with purified water to bind Cu$^{2+}$ with the gel. The Cu$^{2+}$ liberated in the column was washed with 50 mM Tris-HCl buffer, pH 7.0, or 50 mM sodium phosphate buffer, pH 6.0, containing 0.5M sodium chloride and a Chelating Sepharose FF Column ($\phi$5×20 cm, 4 ml, Pharmacia) not bound with Cu$^{2+}$ was connected next to said column, followed by equilibration with the same buffer.

A sample (1 ml, 118 mg/ml, A$_{350}$/A$_{280}$=0.0258) containing purified r-HSA obtained in the above-mentioned Reference Examples 1 and 3, and the buffer changed to the above-mentioned washing/equilibrating buffer by PD-10 [prepack minicolumn packed with a gel filtration carrier (crosslinked dextrin, trademark Sephadex G25, manufactured by Pharmacia)] was applied to the column prepared in the above and washed with the same buffer (100 ml), and the adsorbed component was separated and eluted by the linear gradient method, while increasing the concentration of ammonium chloride, with the use of the same buffer (200 ml) containing 2.00M ammonium chloride (flow rate 1.0 ml/min., 14 ml/cm²/hr).

HSA concentration and $A_{350}/A_{280}$ value of each eluted fraction were determined by the method described in the following (a) and the concentration of the component derived from yeast was determined by the method described in the following (b).

Determination methods (a) Gel filtration analysis by HPLC

The sample (50 µl) was injected into a TSKgel G3000SW$_{XL}$ column equilibrated in advance with 50 mM sodium phosphate buffer, pH 6.5, containing 0.1% sodium azide and 0.3% sodium chloride. The sample component was separated at a flow rate of 1 ml/min using the same buffer as an eluent. The detection was done at $A_{280}$ and $A_{350}$. The albumin concentration in the sample was calculated in a relative manner using the peak height of 2.5 mg/ml albumin derived from plasma.

(b) Determination by ELISA of the component derived from yeast

An antibody solution diluted 960-fold with 50 mM carbonate buffer (pH 9.6) was added to a plate by 100 µl/well and allowed to stand for one day at room temperature. The plate was washed once with a 0.9% NaCl solution containing 0.05% Tween 20, added with PBS containing 1% skimmed milk by 200 µl/well, and allowed to stand at room temperature for 2 hr.

The plate was washed once with a 0.9% NaCl solution containing 0.05% Tween 20, added with a sample by 50 µl/well, and allowed to stand at 37° C. for 3 hr.

The plate was washed 6 times with a 0.9% NaCl solution containing 0.05% Tween 20, added with a biotin-antibody solution diluted 10,000-fold with PBS containing 1% skimmed milk, by 50 µl/well, and allowed to stand at 37° C. for 2 hr.

The plate was washed 6 times with a 0.9% NaCl solution containing 0.05% Tween 20, added with an avidin-HRP (horseradish peroxidase) solution diluted 1,000-fold with PBS containing 1% skimmed milk, by 50 µl/well, and allowed to stand at 37° C. for 1 hr.

The plate was washed 6 times with a 0.9% NaCl solution containing 0.05% Tween 20, added with a substrate by 50 µl/well, and allowed to stand for 30–60 min at room temperature. 2N Sulfuric acid (50 µl/well) was added to stop the reaction and $A_{490}$ of each well was determined.

A standard curve was drawn from the data obtained by adding a known amount of the component derived from yeast instead of a sample, based on which the amount of the component derived from yeast, which was contained in the sample, was determined.

Figure 2B:
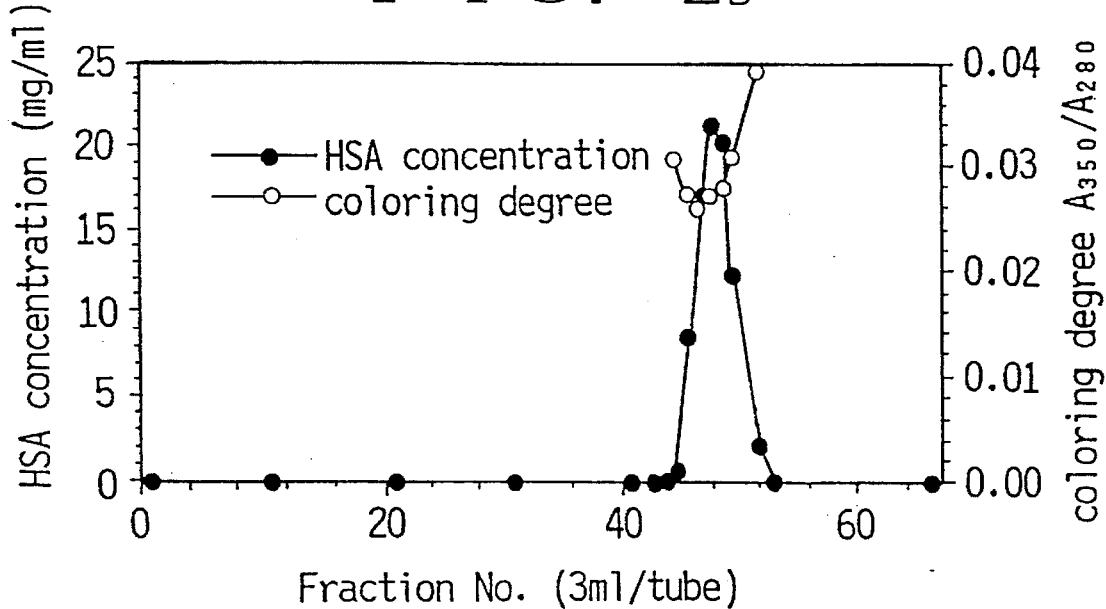

An r-HSA monomer concentration and concentration of the component derived from yeast in each eluted fraction are shown in FIG. 1. Also, an r-HSA monomer concentration and $A_{350}/A_{280}$ value of each eluted fraction are shown in FIG. 2.

The r-HSA and the component derived from yeast were wholly adsorbed in the column in the absence of an antagonist. Both the adsorbed components were eluted with the increasing concentrations of the antagonist (ammonium chloride), and the peak of HSA appeared in the lower concentration region than did the peak of the component derived from yeast. The two peaks were considerably apart, showing superior separation property.

Example 2

A 5 mg/ml CuSO$_4$ solution was poured on a Chelating Sepharose FF Column (φ16 ×5 cm, 10 ml) previously washed with purified water to bind Cu$^{2+}$ with the gel. The Cu$^{2+}$ liberated in the column was washed with 50 mM sodium phosphate buffer, pH 6.0, containing 0.5M sodium chloride and ammonium chloride at various concentrations (1.8M, 2.1M, 2.4M), and a Chelating Sepharose FF Column (φ5×5 cm, 1 ml) not bound with Cu$^{2+}$ was connected next to said column, followed by equilibration with the same buffer.

A sample (2 ml, 144 mg/ml, $A_{350}/A_{280}$=0.0253) containing purified r-HSA obtained in the above-mentioned Reference Examples 1 and 3, and the buffer changed to the above-mentioned washing/equilibrating buffer by the use of PD-10 (mentioned earlier) was applied to the column prepared in the above and washed with the same buffer (98 ml). The component which was not adsorbed by chelating chromatography was collected (flow rate 0.5 ml/min., 7 ml/cm₂/hr).

In the same manner as in Example 1, HSA concentration was determined by HPLC and the concentration of the component derived from yeast was determined by ELISA. The results are shown in Table 4.

TABLE 4

Purification of r-HSA by Cu-chelating chromatography

| NH$_4$Cl (M) | Recovery (%) | Yeast-derived component/ HSA | $A_{350}/A_{280}$ |
|---|---|---|---|
| Test sample | — | $1.11 \times 10^{-7}$ | 0.0253 |
| 1.8 | 51 | $1.95 \times 10^{-9}$ | 0.0237 |
| 2.1 | 68 | $2.92 \times 10^{-9}$ | 0.0249 |
| 2.4 | 93 | $2.78 \times 10^{-9}$ | 0.0241 |

The recovery ratio of r-HSA increased with increasing ammonium chloride concentrations, and the ratio was 93% in the system using 2.4M ammonium chloride.

The purity was presented by the ratio of the concentration of the component derived from yeast relative to the concentration of r-HSA monomer. When compared with the purity before the chelating chromatography treatment, an improvement in the purity of the order of approximately two was found in all three systems.

What is claimed is:

1. A method of removing contaminant components of the host cell that produces recombinant human serum albumin, which comprises treating a fraction containing the recombinant human serum albumin, by Cu-chelating chromatography.

2. The method of claim 1, comprising eluting a component of the fraction containing the recombinant human serum albumin which has been adsorbed by Cu-chelating chromatography, with a buffer containing ammonium chloride and having a pH of about 5–7.

3. The method of claim 1, wherein the Cu-chelating chromatography comprises the steps of:
   (a) bringing the fraction containing the recombinant human serum albumin into contact with a chelating chromatography carrier bound with copper ions, and
   (b) eluting the human serum albumin adsorbed by the carrier with a buffer containing an antagonist and having a pH of about 5–7.

4. The method of claim 3, wherein the antagonist is selected from the group consisting of ammonium chloride, imidazole, histidine, cysteine, glycine and histamine.

5. The method of claim 4, wherein the antagonist is ammonium chloride.

6. The method of claim 5, wherein the buffer contains 1–3M ammonium chloride.

7. The method of claim 3, wherein a ligand of the chelating chromatography carrier is iminodiacetic acid.

8. The method of claim 1, wherein the Cu-chelating chromatography comprises the steps of:
   (a) bringing the fraction containing the recombinant human serum into contact with a chelating chromatography carrier bound with copper ions, which has been equilibrated with a buffer containing an antagonist and having a pH of about 5–7, and
   (b) collecting an unadsorbed fraction.

9. The method of claim 8, wherein the antagonist is selected from the group consisting of ammonium chloride, imidazole, histidine, cysteine, glycine and histamine.

10. The method of claim 9, wherein the antagonist is ammonium chloride.

11. The method of claim 10, wherein the buffer contains 1–3M ammonium chloride.

12. The method of claim 8, wherein a ligand of the chelating chromatography carrier is iminodiacetic acid.

13. The method of claim 1, comprising the following steps of purification before the treatment by Cu-chelating chromatography:

(1) treatment of the fraction containing the recombinant human serum albumin, using ultrafiltration membranes having a fractional molecular weight of 100,000–500,000 and 1,000–50,000;

(2) heat treatment at 50°–70° C. for 30 minutes to 5 hours;

(3) treatment with an acid at a pH of 3–5;

(4) treatment using an ultrafiltration membrane having a fractional molecular weight of 100,000–500,000;

(5) contacting the fraction with a cation exchanger under the conditions of pH 3–5 and a salt concentration of 0.01–0.2M and then eluting under the conditions of pH 8–10 and a salt concentration of 0.2–0.5M;

(6) contacting the eluate with a carrier for hydrophobic chromatography under the conditions of pH 6–8 and a salt concentration of 0.01–0.5M to collect an unadsorbed fraction; and (7) contacting the fraction with an anion exchanger under the conditions of pH 6–8 and a salt concentration of 0.01–0.1M to collect an unadsorbed fraction.

* * * * *